United States Patent [19]
Pfreundschuh

[11] Patent Number: 6,025,191
[45] Date of Patent: Feb. 15, 2000

[54] ISOLATED NUCLEIC ACID MOLECULES WHICH ENCODE A MELANOMA SPECIFIC ANTIGEN AND USES THEREOF

[75] Inventor: Michael Pfreundschuh, Homburg/Saar, Germany

[73] Assignee: Ludwig Institute for Cancer Research, New York, N.Y.

[21] Appl. No.: 08/580,980

[22] Filed: Jan. 3, 1996

Related U.S. Application Data

[63] Continuation-in-part of application No. 08/479,328, Jun. 7, 1995, Pat. No. 5,698,396.

[51] Int. Cl.⁷ .............................. C12N 15/11; C12N 5/00
[52] U.S. Cl. ....................... 435/320.1; 435/325; 536/23.1
[58] Field of Search ........................ 536/23.1; 436/320.1, 436/325

[56] References Cited

U.S. PATENT DOCUMENTS 4,889,806  12/1989  Olson et al. ........................ 435/172.3

OTHER PUBLICATIONS

Clark et al (Nature Genet. 1994, 7(4)–502–508.
Sambrook et al (Molecular Cloning, A Laboratory Manual, Cold Spring Harbor, 1989, pp p. 16.3–4.

*Primary Examiner*—Lila Feisee
*Assistant Examiner*—Susan Ungar
*Attorney, Agent, or Firm*—Felfe & Lynch

[57] ABSTRACT

The invention involves the isolation of a nucleic acid molecule which encodes a melanoma associated antigen. Cell lines and expression vectors which include this and related sequences, as well as uses of these molecules, are described.

8 Claims, 4 Drawing Sheets

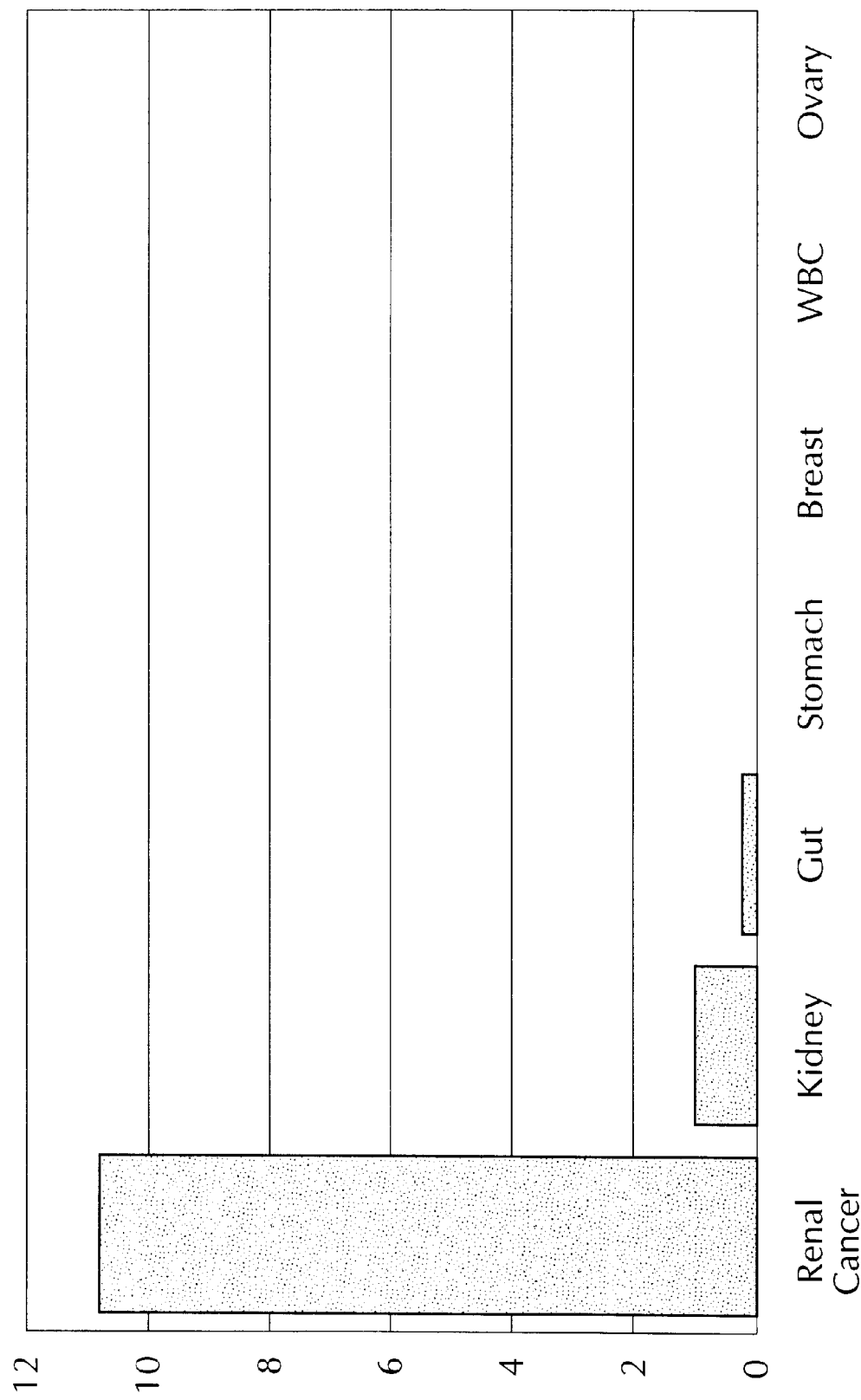

FIG. 4

```
ORIGIN
   1 ATCTGCAGAA TTCGGCTTCG ATCTAGAACT AGTGGATCCC CCGGGCTGCA GGAATTCGGC
  61 ACGAGCGGTT CCAAGTGGAC TTATTTTGGT CCTGATGGGG AGAATAGCTG GTCCAAGAAG
 121 TACCCGTCGT GTGGGGGCCT GCTGCAGTCC CCCATAGACC CAAGGCTACA TGCACAGTGA CATCCTCCAG
 181 TATGACGCCA GCCTCACGCC CCTCGAGTTC CAAGGCTACA ATCTGTCTGC CAACAAGCAG
 241 TTTCTCCTGA CCAACAATGG CCATTCAGTG AAGCTGAACC TGCCCTCGGA CATGCACATC
 301 CAGGGCCTCC AGTCTCGCTA CAGTGCCACG CAGCTGCACC TGCACTGGGG GAACCCGAAT
 361 GACCCGCACG GCTCTGAGCA TACCGTCAGC GGACAGCACT TCTCCGCCGA GCTGCACATT
 421 GTCCATTATA ACTCAGACCT TTATCCTGAC GACAG?ACTG CCAGCAACAA GTCAGAAGAC
 481 CTCGCTGTCC TGGGTGCTCT CATTGAGATG GGCTCCTTCA ATCCGTCCTA TGACAAGATC
 541 TTCAGTCACC TTCAACATGT AAAGTACAAA GGCCAGGAAG CATTCGTCCC GGGATTCAAC
 601 ATTGAAGAGC TGCTTCCGGA GAGGACCGCT GAATATTACC GCTACCGGGG GTCCCTGATC
 661 ACACCCCCTT GCAACCCCAC TGTGCTCTGG ACAGTTTTCC GAAACCCCGT GCAAATTTCC
 721 CAGGAGCAGC TGCTGGCTTT GGAGACAGCC CTGTACTGCA CACACATGGA CGACCCTTCC
 781 CCCAGAGAAA TGATCAACAA CT?CCGGCAG GTCCAGAAGT TCG?TGAGAG GCTGTGTATAC
 841 ACCTCCTTCT C?CAAGTGCA AGTCTGTACT GCGGCAGGAC TGAGTCTGGG CATCATCCTC
 901 TCACTGGCCC TGGCTGGCAT TCTTGGCATC TGTATTGTGG TGGTGGTGTC CATTTGGCTT
 961 TTCAGAAGGA AGAGTA?CCC C?AAAGGTGA TAACAAGGGA GTCATTTACA AGCCA?CCAC
1021 CAAGATGGAG ACTGAGGCCC ACGCTTGAGG TCCCCGGAGC TCCCGGGCAC ATCCAGGAAG
1081 GACCTTGCTT TTGGACCCTA CACACACTCG CTCTCTGGAC ACTTGCGACA CCTCAAGGTG
1141 TTCTCTGTAG CTCAATCTGC AAACATGCCA GGCCTCAGGG ATCCTCTGCT
//
```

ISOLATED NUCLEIC ACID MOLECULES WHICH ENCODE A MELANOMA SPECIFIC ANTIGEN AND USES THEREOF

RELATED APPLICATION

This application is a Continuation-in-part of application Ser. No. 08/479,328, filed on Jun. 7, 1995, now U.S Pat. No. 5,698,396.

FIELD OF THE INVENTION

This invention relates to methodologies for identifying molecules of interest. In particularly preferred embodiments, the invention relates to the identification of molecules associated with pathological conditions such as cancer, (melanoma or renal cancer, e.g.), Hodgkin's Disease, autoimmune diseases and so forth. Also a part of the invention are the isolated molecules found as a result of the inventive method. These molecules include, inter alia, protein-containing molecules, isolated nucleic acid molecules encoding these, and antibodies which specifically bind to the protein-containing molecules. For convenience, the method described herein will be referred to as "serological fishing".

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding molecule to express the desired molecule.

To date, two strategies have been employed for the detection of such antigens, in, e.g., human tumors. These will be referred to as the genetic approach and the biochemical approach. The genetic approach is exemplified by, e.g., dePlaen et al., Proc. Natl. Acad. Sci. USA 85: 2275 (1988), incorporated by reference. In this approach, several hundred pools of plasmids of a cDNA library obtained from a tumor are transfected into recipient cells, such as COS cells, or into antigen-negative variants of tumor cell lines which are tested for the expression of the specific antigen. The biochemical approach, exemplified by, e.g., Falk et al., Nature 351: 290 (1991), and Kawakami et al., Nature 369: 69 (1994) both of which are incorporated by reference, is based on acidic elution of peptides which have bound to MHC-I molecules of tumor cells, followed by reversed-phase high performance liquid chromotogaphy (HPLC). Antigenic peptides are identified after they bind to empty MHC-I molecules of mutant cell lines, defective in antigen processing, and induction of specific reactions in cytolytic T-lymphocytes. These reactions include induction of CTL proliferation, TNF release, and lysis of target cells, measurable in an MTT assay, or a $^{51}Cr$ release assay.

These two approaches to the molecular definition of antigens have the following disadvantages: first, they are enormously cumbersome, time-consuming and expensive; second, they depend on the establishment of cytolytic T cell lines (CTLs) with predefined specificity; third, their relevance in vivo for the course of the pathology or disease in question has not been proven, as the respective CTLs can be obtained not only from patients with the respective disease, but also from healthy individuals, depending on their T cell repertoire.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643–1647 (1991); Brichard et al., J. Exp. Med. 178: 489–495 (1993); Coulie, et al., J. Exp. Med. 180: 35–42 (1994), Kawakami et al., Proc. Natl. Acad. Sci. USA 91: 3515–3519 (1994).

It would be desirable to have available a method which can be used not only for detection of tumor-associated antigens, but to determine molecules associated with any abnormal or pathological condition. Such a method would also facilitate the identification of such molecules, thereby enabling their use on the generation of, e.g., antibodies, cytolytic T cells, and so forth.

It is therefore the purpose of the present invention to develop a method for the simple detection and molecular characterization of antigens in human tissues, especially in tumor cells, which are useful in the molecular diagnosis of diseases and/or for immunotherapy and gene therapy of infectious, autoimmune and malignant diseases. The invention is delineated in the disclosure which follows.

BRIEF DESCRIPTION OF THE FIGURES

FIG. 3 shows, in bar graph form, the Northern Blot analysis of clone HOM-RCC-313 in renal cell carcinoma, normal kidney and other human tissues.

FIG. 4 shows the translated region of the gene coding for HOM-RCC-313.

DETAILED DESCRIPTION OF PREFERRED EMBODIMENTS

Figure 1:
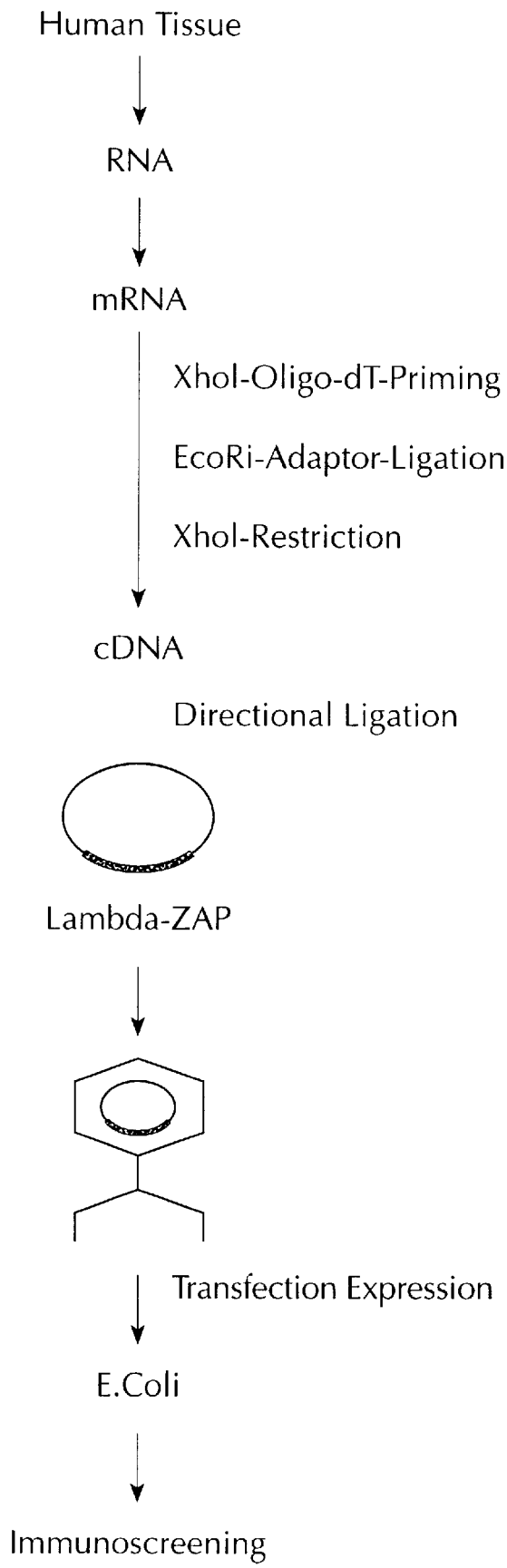
FIG. 1 shows the principles of the approach of the invention.

The following disclosure describes a methodology referred to as serological fishing. In it, a cell sample is taken from a subject afflicted with a pathological condition. The cells preferably are exemplary of the pathology. For example, if the subject has melanoma, the cells are melanoma cells. If the subject is suffering from a neural disorder, e.g., then the cells are preferably a sample of the afflicted cells. This approach is warranted because the afflicted cells are most probably the best source of protein-containing molecules of interest, i.e., such molecules which are specifically associated with the pathological condition of interest.

Note that cells representative of pathological conditions are not the only cells which may be used in the inventive method. It is very important, e.g., to ascertain those cellular "markers" associated with differentiation and maturation of cells, for example. The example of hematopoietic stem cells comes to mind. Similarly, the invention contemplates the isolation of, e.g., receptor molecules for specific ligands. In effect, one can assay for the presence of any molecule of interest using this methodology.

The cells chosen are then used to prepare a library of complementary DNA (i.e., "cDNA"). This methodology is well known to the skilled artisan, and need not be reiterated here. It is, of course, based upon the established fact that if proteins are expressed by the cells, then messenger RNA (mRNA) must be present. These mRNA molecules are not long lived, and are unstable, so they are not practical to work with. The stability brought to the molecules when cDNA is used is very helpful to the method.

Once the cDNA is made, it is used to construct a vector library. In short, carrier vectors are treated, such as by cutting and splicing, to receive molecules of cDNA. The choice of vector may vary, as the skilled artisan is well familiar with many such examples.

Especially preferred are virus based vectors. In the case of eukaryotic cells, retrovirus or adenovirus based vectors are preferred. Such vectors contain all or a part of a viral genome, such as long term repeats ("LTRs"), promoters (e.g., CMV promoters, SV40 promoter, RSV promoter), enhancers, and so forth. When the host cell is a prokaryote, bacterial viruses, or phages, are preferred. Exemplary of such vectors are vectors based upon, e.g., lambda phage. In any case, the vector may comprise elements of more than one virus.

The resulting vectors are transfected or transformed into a host cell, which may be eukaryotic or prokaryotic.

Any cell normally used for transfection or transformation may be used in the protocol. Preferred materials include strains of *E. coli*, CHO cells such as CHO-1, COS cells such as COS-7, and so forth. Similarly, yeast cells, e.g., strains of Saccharomyces, strains of Pseudomonas, such as strains of *Pseudomonas aeruginosa*, Bacillus bacteria, *Spodoptera frugiperda*, a well known insect host cell, and so forth, may all be used.

Once the recipient cells receive the vectors, they are cultivated so as to express foreign, protein containing molecules. "Protein-containing" is used herein because, while prokaryotes express only proteins, eukaryotic cells are well known for their ability to post-translationally modify proteins, so as to produce glycoproteins, lipoproteins, e.g. It must also be borne in mind that "protein containing" as used herein, also encompasses peptides, such as the peptides presented by MHC molecules.

The processes now described below take place independently of the process described above, and no chronological relationship between the two facets of the invention is intended.

In pathological conditions such as cancer and, e.g., autoimmune diseases, there is some immune reaction to molecules associated with the pathology. This reaction can include an antibody response, B cell proliferation, proliferation of specific T cell subpopulations, increases in cytokine production, and so forth. The molecules and cells associated with the response may be found in body fluids of a subject, such as his or her serum. The immune responders will react with the molecule of interest whether it is produced recombinantly or autologously. The problem is to find them. As the examples show, this is done in a unique way. First, the body fluid, or other sample of interest, is reacted with a sample of the same host cells used for transfection or transformation. In this first step, the host cells are not transfected or transformed. The effect of this is to strip any immunogenic binding partners specific for the host cell rather than the targeted molecule. This step is necessary because, as was pointed out, supra, the host cell may be one against which the subject has developed an immune respone at some point. This first stripping removes these immune components.

A second stripping step is then carried out. In this step, the previously stripped sample is now reacted with a sample of the same host cell as was described supra, this time having been transfected or transformed with the carrier vector lacking cDNA from the subject. The reason for this second stripping step is an observation made by the present inventors not reported in the literature. The materials used as vectors, such as phages, viruses, etc., are useful because they naturally infect cells. Thus, *E. coli*, which inhabit the lower intestine of humans, are infected with lambda phage. It had not been considered, previously, that the immune response to *E. coli* includes a response to these infectious agents. Thus, applicants have surprisingly, achieved an ability to remove interfering immune components to an unprecedented degree by carrying out the two stripping steps. As noted, the first is against untransfected or untransformed host cells. The second is against host cells transfected or transformed with a vector which does not carry cDNA, wherein the vector is immunologically equivalent to the vector used to carry cDNA, as described supra.

It is especially preferred to carry out each of these stripping steps using a plurality of similar, but different procedures. The experiments which follow, for example, show absorption on a solid phase column, and then absorption on nitrocellulose paper. Applicants do not wish to be bound by any theory as to why the use of two similar but different protocols produces the results described herein. It is to be borne in mind, hereafter, that whenever "contacting a sample" is used herein, it is not to be limited to one contact step only, but may refer to more than one, preferably different contact protocols designed to remove interfering binding partners from a sample under scrutiny.

It should be understood that these stripping steps may be done completely independently of the steps used to prepare the cDNA library. For example, if the test for an antigen is to be done at day "O", the stripping of sample may be done the day before, a week before, and so forth. One can also "bank" stripped sample from a donor or subject for future use.

The sample used is preferably serum, but need not be. Any sample which contains immunogenic binding partners may be so used.

In the next step of the method, lysed, transfected cells carrying the cDNA and expressing heterologous protein are contacted with the twice stripped sample. This sample should only contain immune components specific for the heterologous protein, and should bind thereto. This binding is facilitated if the cell lysates have been immobilized via contact to, e.g., activated filter paper, a solid phase column, etc., but this solid phase binding is not necessary, as the art will surely recognize that many, varied forms of assays are available for identifying a molecule of interest.

Once the immune component binds to the target molecule, a further step is desirably, but not necessarily, carried out. This additional step involves the use of some binding partner for the first immune component, such as anti-IgG, carrying an identifiable label. The label may be a dye, an enzyme, a gold particle, a radiolabel, or any of the standard labels used in immunoassays.

Once identification is carried out, the immune components are removed, leaving the target molecule. The target molecule is then studied, using any of the standard methodologies in the art.

The artisan will note that the methodology also results in isolation of immune components which bind to the molecule of interest. Thus, in another aspect of the invention one can isolate antibodies, e.g., which are specific binding partners for the molecule of interest.

Yet another immune component which may be identified and isolated following the invention is a cytolytic T cell ("CTL" hereafter), specific for complexes of peptides derived from the identified molecule and MHC molecules to which these peptides bind, forming a complex. It is fairly well accepted that a CTL response involves the identification of complexes of MHC molecules and peptides, generally about 8–12 amino acids in length, but most preferably 9 or 10 amino acids in length, by T cell receptors ("TCRs") on the surface of circulating T cells. The TCRs react by binding to these complexes, setting in motion as it were a series of reactions including the proliferation of CTLs specific for these complexes. One can produce and/or isolate such CTLs using the method of the invention, plus further steps.

As is pointed out in the examples which follow as well as the disclosure in general, one can easily identify cDNA encoding an antigen of interest. Once this is identified, one uses the cDNA to transfect host cells which either already present desired MHC molecules on their surface, or which have been transfected with DNA encoding these MHC molecules. The cDNA for the molecule of interest is expressed, and the molecule is processed to antigenic peptides which are presented by MHC molecules, such as HLA molecules. CTLs directed against the complexes are obtained from lymphocytes, such as autologous lymphocytes. From responder cell populations, long-term CTL clones are then obtained by the well known technique of limiting dilution. Once a positive CTL response is observed, the specific peptides presented to the CTLs are identified using established methods for example, screening the specific of previously identified CTL clones. Alternatively, the more recently described method of studying the sequence of the molecule of interest to identify potential MHC-binding motifs then analyzing these peptides, first for binding to the relevant MHC molecule and then, if positive for MHC-binding, for their ability to generate CTLs recognizing the peptide MHC complex. Of course the peptides can also be eluted from the cells and sequenced, using well known techniques.

It will also be noted by the skilled artisan that one can correlate the expression of the molecule of interest back to a particular host cell or cells which expressed it. In so doing, one can remove the cDNA which expressed the molecule of interest, sequence it, and so forth. This aspect of the method is another feature of the invention.

Specific embodiments of the invention will be seen in the examples which follow. FIG. 1 depicts the method generally.

EXAMPLE 1

For the establishment of a cDNA library from human tissue total RNA was obtained from 0.5 g of a renal clear cell carcinoma and established according to the method of Chomzynski, J. Analyt. Biochem. 162: 156–159 (1987), incorporated by reference. The mRNA was extracted from total RNA with oligo-dT-cellulose. The synthesis of the first strand cDNA was accomplished by the method described by Gubler and Hoffmann, Gene 25: 263 (1983) using RNase H and DNA polymerase I. For adaptation of the cDNA Klenow enzyme, adaptors with EcoRI restriction enzyme sites were ligated to the cDNA ends using T4 DNA ligase (Ferretti V and Sgamerella V, Nucl. Acids Res. 9: 3695 (1981)). Following restriction enzymatic digestion with the enzyme XhoI, cDNA molecules of different length were separated using Sephacryl 400 and transfected into λZAPII phage vectors (Short et al., Nucleic Acids Res. 16: 7583 (1988)). The recombinant phage DNA was packed into phages after ligation with packing extracts and used for the transfection of E. coli bacteria. The titration of the library resulted in $1.8 \times 10^6$ recombinant primary clones. The total cDNA library was transfected in E. coli and amplified. The titer of the cDNA library after amplification was $10^{11}$ plaque forming units per ml (pfu/ml). These transfected cells were used in experiments which follow.

EXAMPLE 2

In accordance with the invention as described, supra, identification of immunogenic material was achieved by using human sera which have been completely depleted of antibodies directed against antigens derived from native and lytic λ phage-transfected E. coli bacteria. To this end, the serum was "stripped" via absorption, as now described.

E. coli bacteria of the strain XL1-blue were cultured in 50 ml LB medium overnight. After achieving an optical density of $OD_{600}=1.0$, the bacteria were pelleted by centrifugation, resuspended in 5 ml phosphate buffered saline (PBS), and sonificated by ultrasound. The bacterial lysate was bound onto a matrix of activated Sepharose, which was then put into a column and used for the absorption of the human serum. The serum was run over this column 10 times.

A culture of E. coli XL1 blue bacteria in the exponential growth phase was pelleted by centrifugation, transfected in 0.01 M magnesium sulfate with $10^6$ λZAPII phages without a recombinant insert and incubated in 5 ml LB medium for four hours. The lysate of the transfected bacteria was used in the same manner as the untransfected bacteria, with the human serum described supra being passed through the column an addition ten times.

To complete the depletion of the serum, interfering antibodies from lytically transfected E. coli bacteria were cultured on agar plates and their proteins were blotted onto nitrocellulose membranes after 10 hours of culture at 37° C.

Following this, the serum which had been preabsorbed according to the above steps was transferred to the blotted nitrocellulose membrane, and the absorption procedure was repeated five times. The serum, which was processed in accordance with the invention, was totally depleted of antibodies directed against antigens derived from *E. coli* and phages.

EXAMPLE 3

In this, a renal cancer-specific antigen was identified via the following steps. Bacteria of the strain *E. coli* XL1 blue were transfected with recombinant phages derived from the described cDNA library and plated at a density of 4–5×10³ plaque forming units (pfu) per plate in LB-medium with isopropylthiogalactopyranoside ("IPTG"). After 12 hours of incubation at 37° C., nitrocellulose membranes were put on top of the cultures and culture plates were incubated for another four hours. This was followed by incubation of the nitrocellulose membrane for one hour in Tris-buffered saline (TBS) with 5% milk powder. After washing the nitrocellulose membranes three times in TBS, the stripped human serum secured following Example 2 was diluted 1:1000 in TBS/0.5% (w/v) milk powder and incubated overnight with gentle shaking. After the incubation with the nitrocellulose membrane the serum was removed and kept for additional testing. Following incubation with serum, the nitrocellulose membranes were washed three times in TBS, and incubated with a polyclonal alkaline phosphatase-conjugated goat anti-human IgG serum for one hour. Following this, the nitrocellulose membranes were washed repeatedly with TBS/0.01% (v/v Tween 20). The reaction was developed using nitroblue tetrazolium chloride and bromochloro-indoyl-phosphate in TBS. The binding of human antibodies to the expressed protein became visible by a blue ring-formed color deposit on the nitro-cellulose membrane. The efficient preabsorption of the serum made it possible to develop the membrane at 37° C. over several hours without compromising the quality of the test because of background reactivity caused by antibodies against *E. coli* and phage antigens.

Positive clones were localized on the agar plates, transferred into transfection buffer, and used for a second round of transfection and subcloning. A total of 1.8×10⁶ recombinant clones were subjected to screening and five different positive-reacting clones were identified.

EXAMPLE 4

Figure 2:
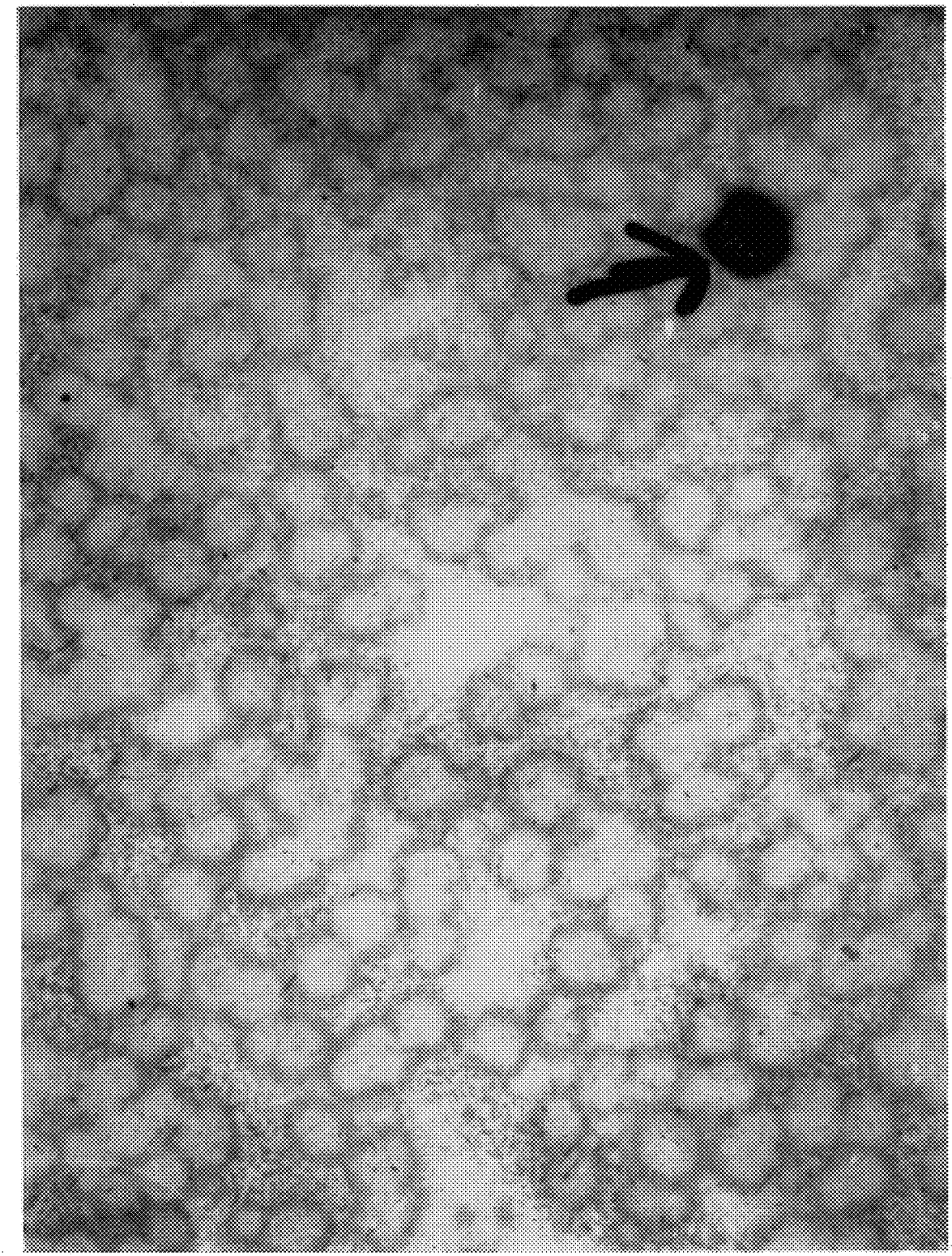
FIG. 2 shows a nitrocellulose membrane with a positive clone derived from the cDNA of a renal cell clear carcinoma that reacts with a 1:100 dilution of the patient's serum.

Positive clones secured following Example 3, i.e., those which had bound antibodies derived from the processed human serum, were subcloned to monoclonality by repeated rounds of transfection and testing of reactivity with the processed human serum. P-bluescript phagemids with the respective cDNA inserts were cloned by in vivo excision (Hay and Short, Strategies 5: 16–19, 1992) from the λZAPII phage vectors and used for the transfection of *E. coli* SOLR bacteria. Plasmids were isolated from the bacteria after alkaline lysis with NaOH in a modification of the method of Birnboim and Doly, J. Nucl. Acids Res. 7: 1513 (1979). The recombinant plasmid DNA was sequenced according to the classic method of Sanger (Proc. Natl. Acad. Sci. USA 74: 5463 (1977)) using M13-forward and M13-reverse oligonucleotides. The DNA sequence obtained and the resulting amino acid sequence were checked for in nucleic acid and protein data banks (Gene Bank, EMBL, Swiss Prot). The sequencing of the cDNA inserts was continued using internal oligonucleotides. Analysis showed no homology with any sequences deposited in the data banks. The full length cDNA clone referred to as SK313, which had been cloned with the RACE method (Frohman M A, Dush M K, Martin G R, Proc. Natl. Acad Sci. USA 85: 8998 (1988)), had a carbonic anhydrase domain at the 5' end. The nucleic acid sequence of this molecule is presented in SEQ ID NO: 1. FIG. 2 shows a nitrocellulose membrane with a positive clone from these experiments.

EXAMPLE 5

As a follow up to these experiments, RNA was isolated from a spectrum of malignant and normal human tissues according to the method of Chomzynski and Sacchi Analyt Biochem. 162: 156 (1987). After denaturation, the total isolated RNA was separated on an agarose gel containing 1% formaldehyde by electrophoresis (Goldberg, Proc. Natl. Acad. Sci. USA 77: 5794 (1980)) and then blotted onto a nylon membrane according to a known method (Seed, Nucl. Acids Res. 10: 1799 (1982)) Radiolabeled cDNA inserts of the identified clones were used for hybridization. The hybridization was carried out according to a known method (Geoffrey & Berger, Enzymol. 152: 419 (1987)). The presence of the respective RNA was demonstrated using autoradiography and X-ray films. The analysis demonstrated that the mRNA of clone HOM-RCC-313 was overexpressed in 4 out of 19 renal cell carcinomas compared to normal kidneys. Very weak expression was found only in colonic mucosal tissue and in normal kidney. Expression in other tissues could not be demonstrated.

EXAMPLE 6

To determine the incidence of antibodies against antigens which are identified in accordance with the invention, sera from healthy individuals and tumor patients were analyzed. To this end, the sera were processed as described, supra, and depleted of antibodies against antigens derived from *E. coli* and phages. For the detection of antigen-specific antibodies, phages derived from reactive clones were mixed with non-reactive phages derived from the same cDNA library at a ratio of 1:10 and tested as described supra for reactivity with antibodies in the human test serum. The serum which had been used for the identification of the antigen was used as a positive clone. The non-reactive phages served as a negative control. A serum sample was positive for antigen reactive antibodies, if the expected percentage of the phage plaques showed a positive reaction. In the case of the renal cell carcinoma antigen represented by clone HOM-RCC-313, the analysis of a spectrum of human sera showed that only sera from renal cell carcinoma patients contained reactive antibodies. Sera from healthy controls and patients with other tumors did not contain such antibodies.

The cDNA for clone HOM-RCC-313 was excised from the plasmid DNA by digestion with the restriction enzyme EcoRI, was separated by agarose gel electrophoresis, followed by extraction from the gel. This was then used to create a vector which expresses a fusion protein with the bacterial protein anthranilate synthetase. A relevant fragment in the exact open reading frame was cloned into pATH plasmid vectors (Koerner, Hill, Myers, Tzagaloff, Meth. Enzymol. 194: 477 (1991). Induction of protein expression was obtained after transformation of the plasmids into *E. coli* of strain BL21 as described (Spindler, Rosser, Berk, J. Virol. 49: 132 (1984)). Expressed, fusion proteins were separated by SDS gel electrophoresis, excised from the gel, eluted and freeze dried. Rabbits were immunized by subcutaneous injection with 100 μg of the lyophilisate dissolved in Freund's adjuvant. Immunization was repeated three times at two-week intervals using incomplete Freund's adjuvant. The rabbit was bled and antiserum was obtained. The obtained antiserum was depleted from antibodies reactive with *E. coli* and phages in the manner described supra and tested for reactivity against the renal carcinoma antigen as described for the human serum. Reactivity was detected at dilutions of 1:>100,000.

EXAMPLE 7

The protocols set forth in the preceding examples were followed, using biopsied tissue taken from different subjects suffering from (i) malignant melanoma, (ii) astrocytoma, and (iii) Hodgkin's Disease. Table 1, which follows, summarized the results, including those obtained with the renal cancer study, set out in detail in Examples 1–6, supra.

TABLE 1

Antibody reactivity of autologous sera with recombinant clones derived from human tumor CDNA. cDNA libraries were screened with autologous patient serum. Positive clones were subcloned to monoclonality. Inserts from each clone were amplified with plasmid primers and separated by agarose gel electrophoresis. Southern blots were performed by cross hybridization with the respective inserts.

| tumor | clones tested | positive clones | different inserts |
|---|---|---|---|
| malignant melanoma | $1.0 \times 10^6$ | 40 | 10 |
| renal cell carcinoma | $1.8 \times 10^6$ | 7 | 5 |
| astrocytoma | $1.2 \times 10^6$ | 49 | 5 |
| Hodgkin's disease | $1.0 \times 10^6$ | 14 | 4 |

Following the analysis of the different inserts observed, the melanoma cells expressed the known tumor rejection antigen precursor MAGE-1 (see van der Bruggen et al., Science 254: 1643–7 (1991), incorporated by reference), as well as a new antigen. A portion of the cDNA sequence of this antigen is set forth in SEQ ID NO: 2.

When the astrocytoma study was completed, the observed insert corresponded to the previously described Tegt gene (Old, Canc. Res. 41: 361–375 (1981), incorporated by reference).

When the Hodgkin's Disease study was completed, a previously unknown antigen was isolated, and cDNA encoding it was identified in the library, using standard methods. The antigen is a newly observed, lectin-like structure, a portion of the cDNA for which is set forth in SEQ ID NO: 3. Also observed were antibodies against restin, described by Bilbe, et al, EMBO J 11: 2103–13 (1992). This is an intermediate filament associated protein, expression of which has been shown to be restricted to Hodgkin and Reed-Sternberg cells, as well as cultured monocytes.

EXAMPLE 8

A further study of occurrence of antibodies against the antigens described in Examples 1–7 was carried out. Table 2 summarizes these assays. In these studies, phages from positive clones were mixed with non-reactive phage (ratio:1:10), and then used to transfect bacteria (*e. coli*). Dilutions of patient sera (1:200), were used, in an enzyme linked immunosorbent assay (ELISA), as described supra. "HOM-MEL-40" refers to the new melanoma antigen (SEQ ID NO: 2), while "HOM-MEL-55" refers to MAGE-1 (van der Bruggen et al., supra). "HOM-RCC 3.1.3" is the renal cancer antigen of SEQ ID NO: 1. "HOM-GLO-30.2.1" refers to the previously identified astrocytoma associated antigen, "HOM-HD-21" refers to the new, lectin-like antigen of SEQ ID NO: 3, and "HOM-HD-397" is the previously identified restin antigen.

TABLE 2

Humoral immune responses against human tumor antigens. Phages from positive clones were mixed with nonreactive phages of the cDNA-library at a ratio of 1:10 and used to transfect bacteria. IgG antibodies to the clones were detected with an enzyme-linked assay using sera. n.t.

| antigen identity/homology | HOM-MEL-40* | HOM-MEL-55 MAGE-1 | HOM-RCC-3.1.3* CAH-like | HOM-GLIO-30.2.1 tegt | HOM-HD-21* lectin-like | HOM-HD-397 rectin |
|---|---|---|---|---|---|---|
| melanoma patients | 2/11 | 4/11 | n.t. | n.t. | n.t. | n.t. |
| recal cancer patients | 0/8 | 0/8 | 2/14 | 0/7 | 0/7 | 5/7 |
| astrocytoma patients | 0/10 | 0/10 | 0/11 | 2/13 | 0/11 | 7/11 |
| Hodgkin's patients | 0/10 | 0/10 | 0/17 | 0/17 | 10/18 | 14/17 |
| healthly controls | 0/12 | 0/12 | 0/15 | 0/20 | 0/17 | 12/17 |

The fact that antibodies against the tumor antigens, excepting only restin, were detected, albeit at varying rates, only in the sera of patients diseased with the same type of tumor suggests that tumor growth is essential for the development of a humoral response against tumor antigens.

The reason for the presence of restin in healthy controls is not clear. One may speculate that tolerance against respective antigens might be circumvented, because the antigen may have similar sequences to another antigen, the donor may have premalignant cells, or the antigen may be activated in normal cells under non-malignant conditions, such as viral infections, or other inflammatory processes.

EXAMPLE 9

In order to determine the expression pattern of the newly identified antigens described herein, Northern blot analysis was carried out, using a variety of human tissues.

RNA was extracted from tissue samples (tumor and normal) using the well known guanidium isothiocyanate/phenol/chloroform method of Chomzynski, et al., supra. The RNA integrity was checked via electrophoresis in formalin/MOPS gels. Then, gels containing 40 ug of RNA per lane were blotted onto nylon membranes. These Northern blots were then probed with the cDNA of SEQ ID NO: 1, 2 or 3. Hybridization was with $^{32}$P labelled probes at 42° C., with formamide. The filters were washed at 65° C., at 1×SSC, 0.2% SDS, and exposed for 16 hours. These are "stringent conditions" as defined hereafter. After exposure, filters were stripped and rehybridized with GAPDH.

Table 3 summarizes these results.

may be a frequent characteristic of proteins which elicit autologous B cell responses.

EXAMPLE 10

Further studies were carried out on the HOM-MEL-40 sequence. Using standard genetic analysis techniques, the 5' region of the mRNA for HOM-MEL 40 was shown to have a tyrosine kinase binding domain. This suggests that HOM-MEL-40 may function as a receptor. The 3' portion of the RNA is identical with an RNA molecule for "SSX," a molecule known to be involved in the SYT-SSX translocation in synovial tumors.

EXAMPLE 11

Additional experiments were also carried out to study HOM-MEL 40. Standard Northern blotting showed that, with the exception of testis, HOM-MEL 40 was not expressed in normal tissues. In contrast, it was expressed in 50% of melanomas, 75% of thyroid cancers, 25% of prostate cancers, 20% of gastric cancers, 16% of colorectal cancers, and 12% of the lung cancers tested.

Additional Western blotting work was carried out, showing that antibodies against HOM-MEL 40 were present in 10 of 89 melanoma patients tested, but only 3 out of 49 healthy male subjects.

In yet further studies, it was observed that HLA-A2 positive tumor cells presented a nonamer derived from HOM-MEL. This suggests that HOM-MEL 40 specific vaccines, useful in inducing CTLs, are possible.

As the foregoing shows, the invention relates to a method for determining or isolating an immunoreactive substance.

TABLE 3

Expression pattern of tumor antigens in various tissues (selection). Northern-slot analysis was performed with RNA samples from tumor and normal human tissues matched by hybridization with GAPDH. Expression ratios were calculated after densitometric analysis of autoradiographs. The signal obtained with the normal coutnerpart of the diseased tissue was set to 1. n.t. = not tested;

| antigen identity/homology | HOM-MEL-40* | HOM-RCC-3.1.3* CAH-like | HOM-GLIO-30.2.1 Tegt | HOM-HD-21* Lectin-like |
|---|---|---|---|---|
| kidney | – | 1 | 1.5 | — |
| brain | – | n.t. | 1 | n.t. |
| tossil | – | — | 1 | 1 |
| stomach | – | — | 1.5 | — |
| colon neucosa | – | 0.2 | 1.5 | — |
| breast | – | — | 1.0 | — |
| renal cancer | – | >5 in 4/19 cases | n.t. | — |
|  | – | ≦1 in 15/19 cases |  |  |
| Hodgkins's tissue | n.t. | — | n.t. | >10 |
| astrocytoma | n.t. | n.t. | >5 in 8/12 | — |
|  |  |  | 1 in 4/12 |  |
| melanoma | ++ | — | n.t. | — |

As will be seen the new melanoma associated antigen is strongly expressed in melanoma, but not other tissues. Carbonic-anhydrase-like antigen was strongly expressed in about 20% of renal cell carcinomas, and only weakly in normal renal tissue. Tegt was overexpressed on 8/12 astrocytoma tissues compared to normal brain tissue. The mRNA for the lectin like molecule associated with Hodgkin's disease was increased about ten fold in diseased tonsils as compared to normal tonsils, suggesting that overexpression "Immunoreactive substance" as used herein refers to any material which provokes some form of immune response in the subject which produces it. This response may be based upon either a B cell or a T cell response. Such immunoreactive substances include proteins, peptides, glycoproteins, lipoproteins, peptide containing complexes (e.g., MHC/peptide complexes), antibodies, and so forth. To determine such substances, a cDNA library is prepared from cells of a subject, using well known, standard methods. The cDNA is then inserted into an appropriate vector, such as a eukaryotic cell specific virus or a phage (i.e., a bacterial virus), to form a transfecting/transforming library, which is then incorporated into a host cell. The host cells are treated so that they express the library component (cloned cDNA) they receive. The host cells are then lysed, so that the expressed material is available for further treatment.

The lysed material is then contacted with a "stripped" sample believed to contain an immunogenic binding partner for the immunoreactive substance. "Immunogenic binding partner" as used herein refers to any immune system associated material which binds to the target, i.e., the immunoreactive substance. Such binding partners include, but are not limited to, antibodies, T cells, cytokines, ligands, receptors, and so forth, as well as truncated portions of these molecules, complementary nucleic acid molecules, and so forth. Note that for some of these components, such as T cells, further steps including those recited herein are required.

The stripped sample, as indicated supra, has been treated by contact with both (i) non-transfected or transformed host cells, and (ii) host cells transfected or transformed with vectors which do not contain the pertinent cDNA.

The stripped sample is useful for identifying binding partners for the expressed material because many of the immune components which would otherwise interfere with the specific immunological reaction desired have been removed via the absorption steps described herein.

The identification of the expressed material may be followed by isolation of the cDNA encoding it. One can punch holes through a membrane, such as a nitrocellulose membrane placed on top of Petri dishes containing colonies of host cells, then use an immune reaction to give position on the solid phase. Each colony is based upon limited cDNA transfection, thereby facilitating isolation and identification of relevant cDNA.

The invention also relates to the isolated nucleic acid molecules of SEQ ID NO: 1, 2 or 3, which encode for molecules which are associated with particular conditions. In addition to their role as coding materials, these molecules can also be used as probes to identify cells expressing the relevant antigens, as it has been shown that these cDNA molecules (SEQ ID NO: 1, 2 and 3) are based upon mRNA which translated to the antigen.

Also a part of the invention are isolated nucleic acid molecules, the complementary sequences of which hybridize to one of SEQ ID NO: 1, 2 or 3, and which encode a protein equivalent to those encoded by SEQ ID NO: 1, 2 or 3. "Stringent conditions" as used herein, refers to conditions at least as stringent as hybridization at 50 $\mu$l/cm$^2$ of 3.5× SSC, 1×Denhardt's solution, 25 mM sodium phosphate buffer (pH 7.0), using a $^{32}$P-labelled probe, for 18 hours at 65° C., followed by four washes (one hour, each wash, at 65° C., 2×SSC, 0.1% SDS), and a final wash for 30 minutes at 1.0×SSC 0.2% SDS. The final wash can be changed to 0.5×SSC to 0.2×SSC, or even 0.1×SSC, and SDS can be lowered to 0.1% to increase stringency, if desired.

Other features of the invention will be clear to the skilled artisan and need not be reiterated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

I claim:

1. Isolated nucleic acid molecule which encodes a protein associated with melanoma, said protein having an amino acid sequence identical to the amino acid sequence encoded by SEQ ID NO: 2.

2. The isolated nucleic acid molecule of claim 1, having a nucleotide sequence consisting of the nucleotide sequence set forth in SEQ ID NO: 2.

3. Expression vector comprising the isolated nucleic acid molecule of claim 1, operably linked to a promoter.

4. Expression vector comprising the isolated nucleic acid molecules of claim 2, operably linked to a promoter.

5. Cell line transformed or transfected with the isolated nucleic acid molecule of claim 1.

6. Cell line transformed or transfected with the isolated nucleic acid molecule of claim 2.

7. Cell line transformed or transfected with the expression vector of claim 3.

8. Cell line transformed or transfected with the expression vector of claim 4.

* * * * *

UNITED STATES PATENT AND TRADEMARK OFFICE
CERTIFICATE OF CORRECTION

PATENT NO.      : 6,025,191
DATED           : February 15, 2000
INVENTOR(S)     : Michael Pfreundschuh It is certified that error appears in the above-identified patent and that said Letters Patent is hereby corrected as shown below:

<u>Title page,</u>
Item [74], *Attorney, Agent, or Firm*, change "Felfe & Lynch" to -- Fulbright & Jaworski L. L. P. --.

<u>Column 4,</u>
Line 13, change "repone" to -- response --.

<u>Column 13,</u>
Line 9, change "partner" to -- partners --.

Signed and Sealed this

Third Day of February, 2004

JON W. DUDAS
*Acting Director of the United States Patent and Trademark Office*

SEQUENCE LISTING (1) GENERAL INFORMATION:

(iii) NUMBER OF SEQUENCES:  4

(2) INFORMATION FOR SEQ ID NO:1:

(i) SEQUENCE CHARACTERISTICS:
      (A) LENGTH: 2679 base pairs
      (B) TYPE: nucleic acid
      (C) STRANDEDNESS: double-stranded
      (D) TOPOLOGY: linear (xi) SEQUENCE DESCRIPTION: SEQ ID NO:1:

```
CGCGAAGATG CCCCGGCGCA GCCTGCACGC GGCGGCCGTG CTCCTGCTGG            50

TGATCTTAAA GGAACAGCCT TCCAGCCCGG CCCCAGTGAA CGGTTCCAAG           100

TGGACTTATT TTGGTCCTGA TGGGGAGAAT AGCTGGTCCA AGAAGTACCC           150

GTCGTGTGGG GGCCTGCTGC AGTCCCCCAT AGACCTGCAC AGTGACATCC           200

TCCAGTATGA CGCCAGCCTC ACGCCCCTCG AGTTCCAAGG CTACAATCTG           250

TCTGCCAACA AGCAGTTTCT CCTGACCAAC AATGGCCATT CAGTGAAGCT           300

GAACCTGCCC TCGGACATGC ACATCCAGGG CCTCCAGTCT CGCTACAGTG           350

CCACGCAGCT GCACCTGCAC TGGGGGAACC CGAATGACCC GCACGGCTCT           400
```

-continued

| | |
|---|---|
| GAGCATACCG TCAGCGGACA GCACTTCTCC GCCGAGCTGC ACATTGTCCA | 450 |
| TTATAACTCA GACCTTTATC CTGACGACAG NACTGCCAGC AACAAGTCAG | 500 |
| AAGACCTCGC TGTCCTGGGT GCTCTCATTG AGATGGGCTC CTTCAATCCG | 550 |
| TCCTATGACA AGATCTTCAG TCACCTTCAA CATGTAAAGT ACAAAGGCCA | 600 |
| GGAAGCATTC GTCCCGGGAT TCAACATTGA AGAGCTGCTT CCGGAGAGGA | 650 |
| CCGCTGAATA TTACCGCTAC CGGGGGTCCC TGATCACACC CCCTTGCAAC | 700 |
| CCCACTGTGC TCTGGACAGT TTTCCGAAAC CCCGTGCAAA TTTCCCAGGA | 750 |
| GCAGCTGCTG GCTTTGGAGA CAGCCCTGTA CTGCACACAC ATGGACGACC | 800 |
| CTTCCCCCAG AGAAATGATC AACAACTTCC GGCAGGTCCA GAAGTTCGAT | 850 |
| GAGAGGCTGG TATACACCTC CTTCTCCCAA GTGCAAGTCT GTACTGCGGC | 900 |
| AGGACTGAGT CTGGGCATCA TCCTCTCACT GGCCCTGGCT GGCATTCTTG | 950 |
| GCATCTGTAT TGTGGTGGTG GTGTCCATTT GGCTTTTCAG AAGGAAGAGT | 1000 |
| ATCAAAAAAG GTGATAACAA GGGAGTCATT TACAAGCCAG CCACCAAGAT | 1050 |
| GGAGACTGAG GCCCACGCTT GAGGTCCCCG GAGCTCCCGG GCACATCCAG | 1100 |
| GAAGGACCTT GCTTTGGACC CTACACACTT CGGCTCTCTG GACACTTGCG | 1150 |
| ACACCTCAAG GTGTTCTCTG TAGCTCAATC TGCAAACATG CCAGGCCTCA | 1200 |
| GGGATCCTCT GCTGGGTGCC TCCTTGTCTT GGGACCATGG NCACCCCAGA | 1250 |
| GCCATCCGAT CGATGGATGG GATGCACTCT CAGACCAAGC AGCAGGAATT | 1300 |
| CAAAGCTGCT TGCTGTAATT GTGTGAGATT GTGAAGTGGT CTGAATTCTG | 1350 |
| GAATCACAAA CCAACCATGC TGGTGGGCCA TTAATGGTTG GAAAACACTT | 1400 |
| CCATCCGGGG CTTTGCCAGA GCGTGCTTTC AAGTGTCCTG GAAATTCTGC | 1450 |
| TGCTTCTCCA AGCTTTCAGA CAAGAATGTG CACTCTCTGC TTAGGTTTTG | 1500 |
| CTTGGGAAAC TCAACTTCTT TCCTCTGGAG ACGGGACATC TCCCTCTGAT | 1550 |
| TTCCTTCTGC TATGCAAAAC CTTTAATCTG CACCTTACAN ACTCGGGGAC | 1600 |
| AAATGGGGAC AGGAAGGATC AAGTTGTAGA GNAGAAAAAG AAAACAAGAG | 1650 |
| ATATACATTG TGATATATAT TAGGGACACT TTCACAGTCC TGTCCTCTGG | 1700 |
| ATCACAGACA CTGCACAGAC CTTAGGGAAA TGGCAGGTTC AAAGTTCCAC | 1750 |
| TTCTTGGTGG GGATGAGAAG GGAGAGAGAG CTAGAGGGAC AAAGAGAATG | 1800 |
| AGAAGACATG GATGATCTGG GAGAGTCTCA CTTCGGAATC AGAATTGGAA | 1850 |
| TCACATTCTG TTTATCAAGC CATAATGTAA GGACAGAATA ATACAATAAT | 1900 |
| AAGTCCAAAT CCAACCTCCT GTCAGTGGAA CAGTTATGTT TTATACTCTA | 1950 |
| CAGATTTTAC AAATANATGA GGCTNGTTCC TTGAAAANTG TGTTGNNTTG | 2000 |
| CTGTNGTCCN NTGGAGGAGA CATGAGTTCC GAGATGACCA ACTCNNGCNT | 2050 |
| TGNATNCTNG GAGGNAATAN GGCAGAACCA AAATGACTGT AGAACTTATT | 2100 |
| CTCTGTAGGC CAAATTTCAT TTCAGCCACT TCTGCAGGAT CCTACTGCCA | 2150 |
| ACCTGGAATG GAGACTTTTA TCTACTTCTC TCTCTCTGAA GATGTCAAAT | 2200 |
| CGTGGTTTAG ATCAAATATA TTTCAAGCTA TAAAAGCAGG AGGTTATCTG | 2250 |
| TGCAGGGGGC TGGCATCATG TATTTAGGGG CAAGTAATAA TGGAATGCTA | 2300 |
| CTAAGATACT CCATATTCTT CCCCGAATCA CACAGACAGT TTCTGACAGG | 2350 |
| CGCAACTCCT CCATTTTCCT CCCGCAGGTG AGAACCCTGT GGAGATGAGT | 2400 |

| | |
|---|---|
| CAGTGCCATG ACTGAGAAGG AACCGACCCC TAGTTGAGAG CACCTTGCAG | 2450 |
| TTCCCCGAGA ACTTTCTGAT TGCACAGTCT CATTTTGACA GCATGAAATG | 2500 |
| TCCTCTTGAA GCATAGCTTT TTAAATATCT TTTTCCTTCT ACTCCTCCCT | 2550 |
| CTGACTCTAG GAATTCTCTC TTCTGGAATC GCTTGAACCC AGGAGGCGGA | 2600 |
| GGTTGCAGTA AGCCAAGGTC ATGCCACTGC ACTCTAGCCT GGGTGACAGA | 2650 |
| GCGAGACTCC ATCTCAAAAA AAAAAAAAA | 2679 |

(2) INFORMATION FOR SEQ ID NO:2:

(i) SEQUENCE CHARACTERISTICS:
        (A) LENGTH: 931 base pairs
        (B) TYPE: nucleic acid
        (C) STRANDEDNESS: double-stranded
        (D) TOPOLOGY: linear (xi) SEQUENCE DESCRIPTION: SEQ ID NO:2:

| | |
|---|---|
| ACTTTCTCTC TCTTTCGATT CTTCCATACT CAGAGTACGC ACGGTCTGAT | 50 |
| TTTCTCTTTG GATTCTTCCA AAATCAGAGT CAGACTGCTC CCGGTGCCAT | 100 |
| GAACGGAGAC GACGCCTTTG CAAGGAGACC CACGGTTGGT GCTCAAATAC | 150 |
| CAGAGAAGAT CCAAAAGGCC TTCGATGATA TTGCCAAATA CTTCTCTAAG | 200 |
| GAAGAGTGGG AAAAGATGAA AGCCTCGGAG AAAATCTTCT ATGTGTATAT | 250 |
| GAAGAGAAAG TATGAGGCTA TGACTAAACT AGGTTTCAAG GCCACCCTCC | 300 |
| CACCTTTCAT GTGTAATAAA CGGGCCGAAG ACTTCCAGGG GAATGATTTG | 350 |
| GATAATGACC CTAACCGTGG GAATCAGGTT GAACGTCCTC AGATGACTTT | 400 |
| CGGCAGGCTC CAGGGAATCT CCCCGAAGAT CATGCCCAAG AAGCCAGCAG | 450 |
| AGGAAGGAAA TGATTCGGAG GAAGTGCCAG AAGCATCTGG CCCACAAAAT | 500 |
| GATGGGAAAG AGCTGTGCCC CCCGGGAAAA CCAACTACCT CTGAGAAGAT | 550 |
| TCACGAGAGA TCTGGACCCA AAGGGGGGA ACATGCCTGG ACCCACAGAC | 600 |
| TGCGTGAGAG AAAACAGCTG GTGATTTATG AAGAGATCAG CGACCCTGAG | 650 |
| GAAGATGACG AGTAACTCCC CTCAGGGATA CGACACATGC CCATGATGAG | 700 |
| AAGCAGAACG TGGTGACCTT TCACGAACAT GGGCATGGCT GCGGACCCCT | 750 |
| CGTCATCAGG TGCATAGCAA GTGAAAGCAA GTGTTCACAA CAGTGAAAAG | 800 |
| TTGAGCGTCA TTTTTCTTAG TGTGCCAAGA GTTCGATGTT AGCGTTTACG | 850 |
| TTGTATTTTC TTACACTGTG TCATTCTGTT AGATACTAAC ATTTCATTGA | 900 |
| TGACGAAGAC ATACTTAATC GATATTTGGT T | 931 |

(2) INFORMATION FOR SEQ ID NO:3:

(i) SEQUENCE CHARACTERISTICS:
        (A) LENGTH: 1692 base pairs
        (B) TYPE: nucleic acid
        (C) STRANDEDNESS: double-stranded
        (D) TOPOLOGY: linear (xi) SEQUENCE DESCRIPTION: SEQ ID NO:3:

| | |
|---|---|
| GATCCCCCGG GCTGCAGGAA TTCGGCACGA GCAAAGGACT TCCTAGTGGG | 50 |
| TGTGAAAGGC AGCGGTGGCC ACAGAGGCGG CGGAGAGATG GCCTTCAGCG | 100 |
| GTTCCCAGGC TCCCTACCTG AGTCCAGCTG TCCCCTTTTC TGGGACTATT | 150 |
| CAAGGAGGTC TCCAGGACGG ACTTCAGATC ACTGTCAATG GGACCGTTCT | 200 |

-continued

```
CAGCTCCAGT GGAACCAGGT TTGCTGTGAA CTTTCAGACT GGCTTCAGTG        250

GAAATGACAT TGCCTTCCAC TTCAACCCTC GGTTTGAAGA TGGAGGGTAC        300

TTGGTGTCCA ACACGAGGCA GAACGGAAGC TGGGGGCCCG AGGAGAGGAA        350

GACACACATG CCTTNCCAGA AGGGGATGCC CTTTGACCTC TGCTTCCTGG        400

TGCAGAGCTC AGATTTCAAG GTGATGGTGA ACGGGATCCT CTTCGTGCAG        450

TACTTCACAT CTCGTCATGC CCTGTCCACC GTTGTGGACA CCATCTCCGT        500

CAATGGCTCT GTGCAGCTGT CCTACATCAG CTTCCAGCCT CCCGGCGTGT        550

GGCCTGCCAA CCCGGCTCCC ATTACCCAGA CAGNNNTCAT CCACACAGTN        600

GCAGAGCGCC CNCTGGACAG ATGTCTCTAC TCCCGCCATC CCACCTATGA        650

TGTACCCCCA CCCCGCCTAT CCGATGCCTT TCATCACCAC CATTCTGGGA        700

GGGCTGTACC CATCCAAGTC CATCCTCCTG TCAGGCACTG TNCTGCCCAG        750

TGCTCANGAG GTTCCACATC NAACCTGTGC NCTGGGAACC ACATCGCCTT        800

CCACCTGAAC CCCCGTTTTG ATGAGAATGC TGTGGTCCGC AACACCCAGA        850

TCGACAACTC CTGGGGGTCT CAGGAGCGAA GTCTGCCCCG AAAAATGCCC        900

TTCGTCCGTG GCCAGAGCTT CTCAGTGTGG ATCTTGTGTG AAGCTCACTG        950

CCTCAAGGTG GCCGTGGATG GTCAGCACCT GTTTGAATAC AACCATCGCC       1000

TGAGGAACCT GCCCACCATC AACAGACTGG AAGTGGGGGG CGACATCCAG       1050

CTGACCATGT GCAGACATAG GCGGCTTCCT GGCCCTGGGG CCGGGGCTG        1100

GGGTGTGGGG CAGTCTGGGT CCTCTCATCA TCCCCACTTC CCAGGCCCAG       1150

CCTTTCCAAC CCTGCCTGGG ATCTGGGCTT TAATGCAGAG GCCATGTCCT       1200

TGTCTGGTCC TGCTTCTGGC TACAGCCACC CTGGAACGGA GAAGGCAGCT       1250

GACGGGGATT GCCTCCTCAG CCGCAGCAGC ACCTGGGGCT CCAGCTGCTG       1300

GAATCCTACC ATCCCAGGAY GCAGGCACAG CCAGGGAGAG GGGAGGNGTG       1350

GGCAGTGAAG ATGAAGCCCC ATGCTCAGTC CCCTCCCATC CCCCACGCAG       1400

CTCCACCCCA GTCCCAAGCC ACCAGCTGTC TGCTCCTGGT GGGAGGTGGC       1450

CTCCTCAGCN CCTCCTCTCT GACCTTTAAC CTNACTCTCA CCTTGCACCG       1500

TGCACCAACC CTTCACCCCT CCTGGAAAGC AGGCCTGATG GCTTCCCACT       1550

GGCCTCCACC ACCTGACCAG AGTGTTCTCT TCAGAGGACT GGCTCCTTTC       1600

CCAGTGTCCT TAAAATAAAG AAATGAAAAT NCTTGTTGGC AAAAAAAAA        1650

AAAAAAAAC TCGAGGGGCN NCCCNGTACC CAATTCGCCC TA               1692
```

(2) INFORMATION FOR SEQ ID NO:4:

(i) SEQUENCE CHARACTERISTICS:
        (A) LENGTH: 1190 base pairs
        (B) TYPE: nucleic acid
        (C) STRANDEDNESS: double-stranded
        (D) TOPOLOGY: linear (xi) SEQUENCE DESCRIPTION: SEQ ID NO:4:

```
ATCTGCAGAA TTCGGCTTCG ATCTAGAACT AGTGGATCCC CCGGGCTGCA         50

GGAATTCGGC ACGAGCGGTT CCAAGTGGAC TTATTTTGGT CCTGATGGGG        100

AGAATAGCTG GTCCAAGAAG TACCCGTCGT GTGGGGGCCT GCTGCAGTCC        150

CCCATAGACC TGCACAGTGA CATCCTCCAG TATGACGCCA GCCTCACGCC        200
```

```
CCTCGAGTTC CAAGGCTACA ATCTGTCTGC CAACAAGCAG TTTCTCCTGA       250

CCAACAATGG CCATTCAGTG AAGCTGAACC TGCCCTCGGA CATGCACATC       300

CAGGGCCTCC AGTCTCGCTA CAGTGCCACG CAGCTGCACC TGCACTGGGG       350

GAACCCGAAT GACCCGCACG GCTCTGAGCA TACCGTCAGC GGACAGCACT       400

TCTCCGCCGA GCTGCACATT GTCCATTATA ACTCAGACCT TTATCCTGAC       450

GACAGNACTG CCAGCAACAA GTCAGAAGAC CTCGCTGTCC TGGGTGCTCT       500

CATTGAGATG GGCTCCTTCA ATCCGTCCTA TGACAAGATC TTCAGTCACC       550

TTCAACATGT AAAGTACAAA GGCCAGGAAG CATTCGTCCC GGGATTCAAC       600

ATTGAAGAGC TGCTTCCGGA GAGGACCGCT GAATATTACC GCTACCGGGG       650

GTCCCTGATC ACACCCCCTT GCAACCCCAC TGTGCTCTGG ACAGTTTTCC       700

GAAACCCCGT GCAAATTTCC CAGGAGCAGC TGCTGGCTTT GGAGACAGCC       750

CTGTACTGCA CACACATGGA CGACCCTTCC CCCAGAGAAA TGATCAACAA       800

CTNCCGGCAG GTCCAGAAGT TCGNTGAGAG GCTGGTATAC ACCTCCTTCT       850

CNCAAGTGCA AGTCTGTACT GCGGCAGGAC TGAGTCTGGG CATCATCCTC       900

TCACTGGCCC TGGCTGGCAT TCTTGGCATC TGTATTGTGG TGGTGGTGTC       950

CATTTGGCTT TTCAGAAGGA AGAGTANCCC CNAAAGGTGA TAACAAGGGA      1000

GTCATTTACA AGCCANCCAC CAAGATGGAG ACTGAGGCCC ACGCTTGAGG      1050

TCCCCGGAGC TCCCGGGCAC ATCCAGGAAG GACCTTGCTT TTGGACCCTA      1100

CACACTTCGG CTCTCTGGAC ACTTGCGACA CCTCAAGGTG TTCTCTGTAG      1150

CTCAATCTGC AAACATGCCA GGCCTCAGGG ATCCTCTGCT                 1190
```